United States Patent
Sergoyan

(10) Patent No.: US 6,842,249 B2
(45) Date of Patent: Jan. 11, 2005

(54) CORROSION INHIBITOR COMPOUND PORTABLE DETECTOR

(75) Inventor: Edward G. Sergoyan, Mill Creek, WA (US)

(73) Assignee: The Boeing Company, Seattle, WA (US)

(*) Notice: Subject to any disclaimer, the term of this patent is extended or adjusted under 35 U.S.C. 154(b) by 91 days.

(21) Appl. No.: 10/158,432

(22) Filed: May 29, 2002

(65) Prior Publication Data

US 2003/0223067 A1 Dec. 4, 2003

(51) Int. Cl.⁷ .................................................. G01J 3/50
(52) U.S. Cl. ......................... 356/402; 356/446; 250/226
(58) Field of Search ................................. 356/402, 405, 356/406, 407, 425, 445, 446; 250/226

(56) References Cited

U.S. PATENT DOCUMENTS

| | | | |
|---|---|---|---|
| 4,813,000 A | | 3/1989 | Wyman et al. |
| 5,537,211 A | | 7/1996 | Dial |
| 5,646,735 A | | 7/1997 | Krzyminski |
| 6,111,653 A | * | 8/2000 | Bucknell et al. ............ 356/446 |
| 6,124,936 A | | 9/2000 | Okamoto |
| 2003/0143510 A1 | * | 7/2003 | Berube-Lauziere et al. ... 433/29 |

FOREIGN PATENT DOCUMENTS

WO    WO 99/59462    * 11/1999    ............ A61B/5/00

OTHER PUBLICATIONS

Keyence Corporation of America; RGB Digital Fiberoptic Sensor—CZ Series; 2001; 4 pgs. from website; published on World Wide Web (Internet).

Keyence Corporation, Japan; Instruction Manual Color Recognition Fiberoptic Sensor PI–C92 Series; 1994; 16 pgs.; printed in Japan.

* cited by examiner

Primary Examiner—F. L. Evans
(74) Attorney, Agent, or Firm—Black Lowe & Graham, PLLC; Mark S. Beaufait

(57) ABSTRACT

A portable system is provided for inspecting presence of a coating on a surface. The portable system includes an optical source and a portable optical probe in optical communication with the optical source. The portable optical probe is arranged to access a surface, emit light onto the accessed surface, and receive light reflected by the accessed surface. A portable color discriminator is in optical communication with the portable optical probe and is arranged to discriminate colors of light received by the portable optical probe. A portable logic controller is arranged to determine presence of a coating on the accessed surface responsive to the discriminated colors of the reflected light. Optional configurations of the portable optical probe, including telescopic, 90 degree, and pivoting sensor tips, allow optical inspection of hard-to-reach surfaces as desired.

24 Claims, 8 Drawing Sheets

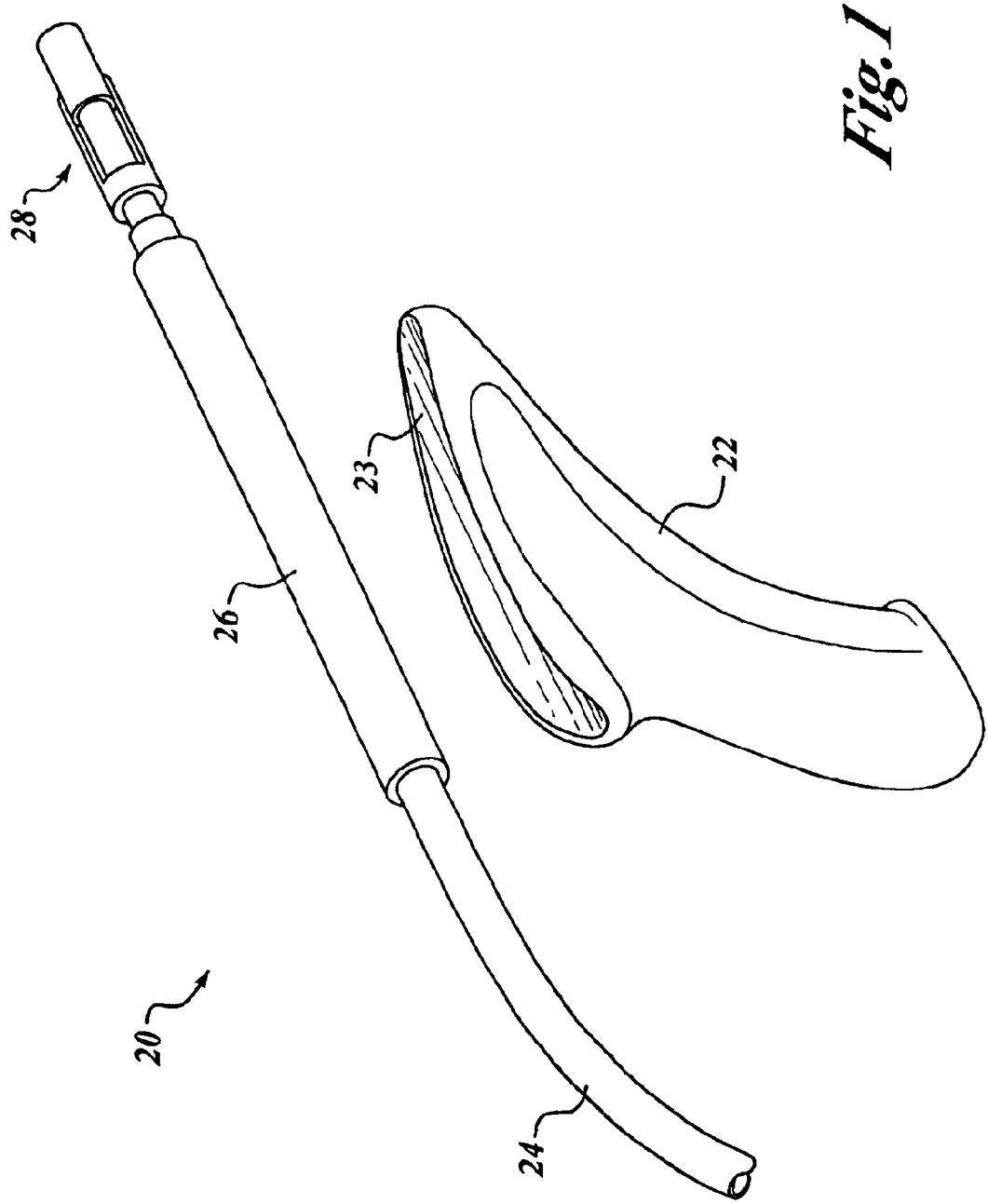

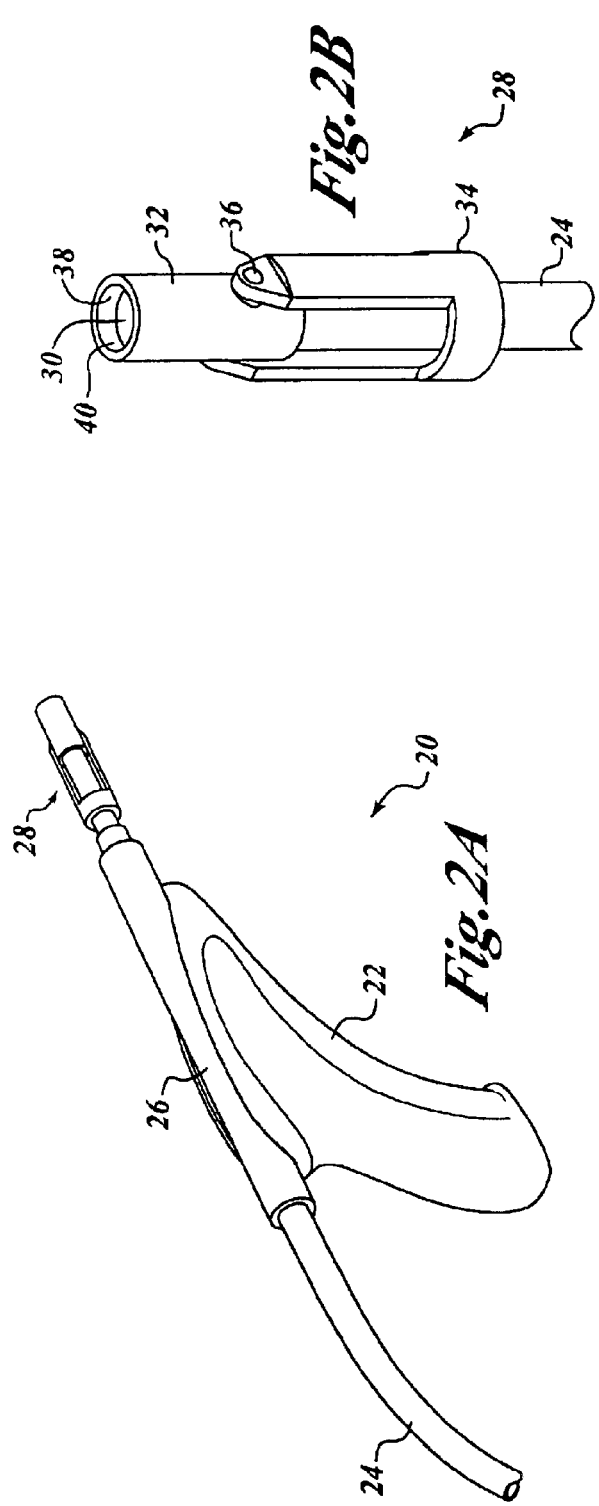
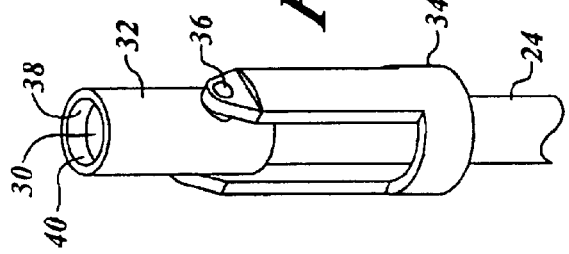
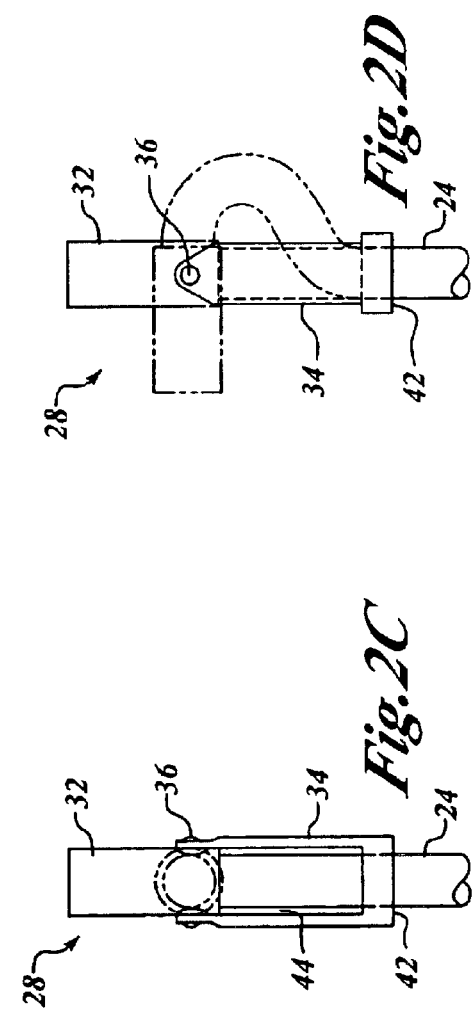
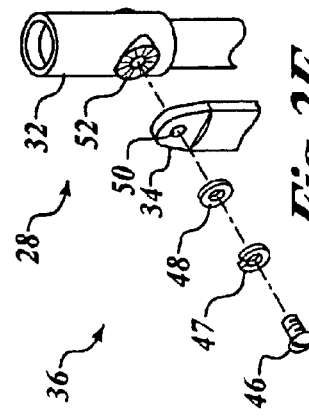

CORROSION INHIBITOR COMPOUND PORTABLE DETECTOR

FIELD OF THE INVENTION

This invention relates generally to coating inspection, and more specifically, to optical coating inspection.

BACKGROUND OF THE INVENTION

Fixed optical devices linked to fixed color discriminators have been used in manufacturing to perform high-speed and highly accurate recognition of target surface colors. This equipment has been typically installed as part of an assembly line using rack mounted equipment and sensors. New optical discriminators allow photoelectric sensors to determine specific colors of the sensed surface unaffected by target gloss, light, and shading. However, such equipment has previously been limited by the size, mounting, and configuration of the sensors and color discriminators.

Equipment and systems, including aircraft that are exposed to the elements, often have their components or assemblages of components coated with corrosion inhibitor compounds. These compounds protect the equipment from the elements and are commonly sprayed on metal components to form a corrosion inhibiting surface. Because corrosion can lead to equipment damage, confirming the presence of corrosion inhibitor compounds on hard-to-reach surfaces is important.

Corrosion inhibitor compounds commonly are semi-translucent. The corrosion inhibitor compound adds a luster to a metal or primed surface that is reflective in a strong light and has a sticky surface tension that can be detected by touch. However, neither the appearance nor the feel of the surface can be inspected easily in hard-to-reach areas. On aircraft, these areas include areas such as the underside of stringers and frames.

The presence of corrosion inhibitor compounds in hard-to-reach areas has previously been checked by hand inspection utilizing a cotton swab. The swab, saturated with a solvent, is dabbed on the hidden area and then the swab is checked for discoloration showing corrosion inhibitor compound. However, this testing requires repair to the tested area. Alternately, to obtain proper coverage by corrosion inhibitor compound in hard-to-reach or hard-to-inspect areas, multiple layers of corrosion inhibitor compound are often applied to ensure that spray-over covers the areas where moisture can settle and corrode a joined surface.

Multiple applications of corrosion inhibitor compounds creates an added expense during manufacturing. Extra applications also add additional weight to the equipment through extra coating thickness and spray accumulation in collection areas. Multiple applications of corrosion inhibitor compound can result in coating thicknesses as much as ten times that required for corrosion protection. In aircraft, as well as other equipment where weight is a factor, multiple applications of corrosion inhibitor compound can result in a significant accumulation of inhibitor compound in bilge areas, increasing weight and thus lifetime equipment expense through increased fuel consumption.

Therefore, there is an unmet need in the art for a portable system for sensing the presence of coatings, especially corrosion inhibiting compounds, in hard-to-reach areas.

SUMMARY OF THE INVENTION

A portable system is provided for inspecting the presence of a coating on a surface. The portable system includes an optical source and a portable optical probe in optical communication with the optical source. The portable optical probe is arranged to access a surface, emit light onto the accessed surface, and receive light reflected by the accessed surface. A portable color discriminator is in optical communication with the portable optical probe and is arranged to discriminate colors of light received by the portable optical probe. A portable logic controller is arranged to determine presence of a coating on the accessed surface responsive to the discriminated colors of the reflected light.

Optional configurations of the portable optical probe, including telescopic, 90 degree, and pivoting sensor tips, allow optical inspection of hard-to-reach surfaces as desired.

The system permits a coatings inspector to quickly and efficiently detect the presence of coatings on hard-to-reach and hidden surfaces. The system is particularly useful for detecting corrosion inhibitor compounds on aircraft, where the prevention of corrosion in joints and recesses is important. Such areas are often hard to access, and the instant invention makes the inspection of these areas comparatively easy to other inspection methods.

BRIEF DESCRIPTION OF THE DRAWINGS

The preferred and alternative embodiments of the present invention are described in detail below with reference to the following drawings:

FIG. 1 is an isometric partially exploded view of a portable optical probe of the present invention;

FIGS. 2A, 2B, 2C, 2D, and 2E show details of the portable optical probe and its sensor tip;

DETAILED DESCRIPTION OF THE INVENTION

Figure 3:
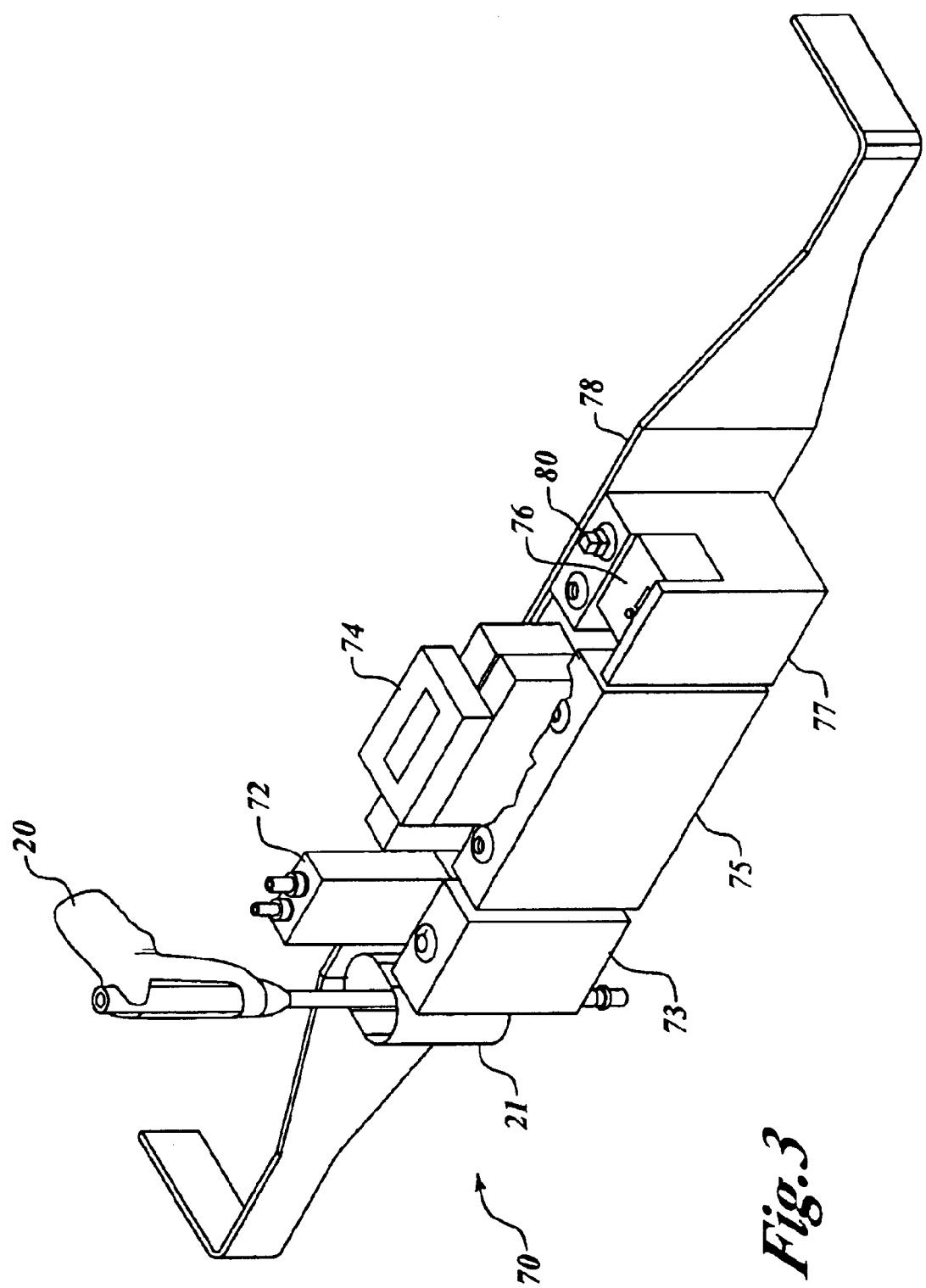
FIG. 3 is a cutaway view of a carrier of the present invention.

By way of overview, a portable system is provided for inspecting presence of a coating on a surface. The portable system includes an optical source and a portable optical probe in optical communication with the optical source. The portable optical probe is arranged to access a surface, emit light onto the accessed surface, and receive light reflected by the accessed surface. A portable color discriminator is in optical communication with the portable optical probe and is arranged to discriminate colors of light received by the portable optical probe. A portable logic controller is arranged to determine presence of the coating on the accessed surface responsive to the discriminated colors of the reflected light. Optional configurations of the portable optical probe, including telescopic, 90 degree, and pivoting sensor tips, allow optical inspection of hard-to-reach surfaces so desired.

FIG. 1 is an isometric view of an exemplary portable optical probe 20 of the present invention. The probe 20 has a detachable handle 22. In the embodiment shown, the handle 22 is pistol grip shaped and defines a recess 23. It will be appreciated that the handle 22 may have any desirable or useful shape. It will also be appreciated that the handle 22 need not be detachable from the probe 20.

The probe 20 is connected to the color discriminator (not shown) through a flexible fiber-optic cable 24. The fiber-optic cable 24 is connected to and threaded through a telescopic extension 26. The telescopic extension is detachably connected to the recess 23 in the handle 22. The telescopic extension 26 is attached to a sensor tip 28. It will be appreciated that the probe 20 may utilize a fixed or flexible extension for the sensor tip 28, and need not have a telescopic extension 26. The sensor tip 28 emits light onto an accessed surface, and receives reflected light from the accessed surface. The sensor tip may suitably be the end of the fiber optic cable 24 alone, or may include a holder for the fiber optic cable, and may include a lense in optical communication with the fiber optic cable 24.

FIGS. 2A and 2B show five detailed views of the probe 20 shown in FIG. 1. FIG. 2A shows the probe 20 with the telescopic extension 26 clipped to the handle 22. The telescopic extension 26 is shown in the collapsed position. The extension 26 tightly clips into the recess 23 in the handle 22 without a separate fastener. It will be appreciated that any suitable device or shapes may be utilized to removably secure the handle 22 to the extension 26, including disconnectable fasteners.

FIG. 2B is a detailed isometric view of the sensor tip 28 of an exemplary embodiment of the present invention. The sensor tip 28 is a pivoting sensor tip. The sensor tip 28 has a pivot tip 32 attached through a pivot 36 to a pivot holder 34. The pivot holder 34 is attached to the telescopic extension 26 (not shown in FIG. 2B). The pivot tip 32 holds and attaches to the fiber-optic cable 24. The fiber-optic cable 24 has a cable end 30. The cable end 30 may be the end of the fiber-optic cable or may be a cable termination or lens that allows light from the optical source (not shown), and returning light from the accessed surface (not shown) to be optically transmitted and received through the cable end 30. The cable end 30 is recessed into the pivot tip 32, thereby defining a sensor recess 38. The pivot tip 32 has a sensor rim 40 which is pressed against the accessed surface (not shown) when the probe is used.

In a present embodiment, the cable end 30 and the fiber optic cable 24 include a bundle of one emitter and six receivers around the emitter. The emitter transmits halogen white light to the accessed surface and the six receivers return the reflected light to the color discriminator (not shown). The fiber-optic cable 24 can have any suitable length. One embodiment of the present invention utilizes a fiber-optic cable 24 approximately 2 meters in length. The configuration of the sensor tip 28 helps to position the cable end 30 at an optimum distance and an optimum angle to the accessed surface. The sensor recess 38 can be defined at different depths. This permits the cable end 30 to be held at a desired distance from the accessed surface when the sensor tip 28 is pressed against the accessed surface. In a present embodiment, the sensor recess is about 10 millimeters in depth.

Depending upon the accessed surface being inspected and the color discriminator being utilized, the optimum angle for sensing coatings with the portable optical probe 20 may vary. The sensor rim 40 of the sensor tip 28 may be parallel to the cable end 30 or may be inclined with respect to the cable end 30 to hold the sensor tip 28 and cable end 30 at an angle to the accessed surface. In one embodiment, the sensor rim 40 is substantially parallel to the cable end 30. In this embodiment, the angle between the accessed surface and the cable end 30 may be adjusted by manually changing the angle of the pivot tip 32 in the pivot holder 34. The inspector may also hold the probe 20 itself at an angle with respect to the accessed surface. In the embodiment shown in FIG. 2B, the pivot tip 32 is substantially perpendicular to the accessed surface when the pivot tip 32 is held such that the sensor tip 40 is tight against the accessed surface. In another embodiment, the optimum angle for sensing coatings on the accessed surface is about 10 degrees from perpendicular to the accessed surface. The sensor rim 40 may be inclined to achieve this sensing angle. In this alternative embodiment, the optimum angle of sensing is achieved by pressing the sensor rim 40 flush against the accessed surface with the sensor rim 40 controlling the sensing angle.

FIG. 2C is a front view of the sensor tip 28 in two alternate positions—one straight and another at 90 degrees. The pivot tip 32 is attached via the pivot 36 to the pivot holder 34. The pivot holder has a cable cutout 44 which allows the fiber-optic cable 24 to project outside of the pivot holder 34 when the pivot tip 32 is pivoted. When the pivot tip 32 is pivoted, the fiber-optic cable 24 slides through the pivot holder 34 through a cable slide 42.

FIG. 2D is a side view of the sensor tip 28 showing the pivot tip 32 in two alternate positions—one straight and another at 90 degrees. When the pivot tip 32 is not straight, the fiber-optic cable 24 projects outside the pivot holder 34 through the cable cutout 44 (not visible in this view).

FIG. 2E is an exploded view of the sensor tip 28 showing details of the pivot 36 that connects the pivot holder 34 to the pivot tip 32. The pivot 36 includes a pivot fastener 46, a washer 47, and a pivot spring 48. The pivot fastener 46 projects through a pivot hole 50, and the pivot fastener 46 is threaded into the pivot surface 52 on the pivot tip 32. The pivot surface 52 is serrated, and the pivot 36 includes a pivot spring 48 to bias the pivot tip 32 in the desired position for sensing. It will be appreciated that alternate embodiments of the invention may utilize any suitable pivot and pivoting surface.

FIG. 3 is a partial cutaway view of a carrier 70 showing the present invention configured for field use. The carrier 70 includes a belt pack 78 including a probe holder 21, a discriminator holder 73, a controller holder 75, and a power system holder 77. In other embodiments, the probe holder 21, the discriminator holder 73, controller holder 75, and power system holder 77, may be combined into one or more holders, and may be different shapes and sizes and made of different materials to hold the present invention. The belt pack 78 and the probe holder 21, discriminator holder 73, controller holder 75, and power system holder 77, are suitably made of heavy fabric. In FIG. 3, the probe holder 21 is configured to conveniently hold the portable optical probe 20. The discriminator holder 73 holds the color discriminator 72. The controller holder 75 holds the portable logic controller 74. The power system holder 77 holds the power system 76. In this embodiment the probe holder 21 is a tube mounted vertically to conveniently holster the portable optical probe 20. The discriminator holder 73, the controller holder 75, and the power system holder 77 are pouches attached to the belt pack 78. In one embodiment, the power system holder 77 also holds a test switch 80 used to activate the present invention. In FIG. 3, wiring between the components, and the fiber-optic cable 24 connecting the probe 20 and the color discriminator 72 are not shown. It will be appreciated that the carrier 70 may have different configurations other than a belt, including without limitation a shoulder pack, a hand carried tool box, a handheld test meter package, a small backpack, or the like.

Figure 4:
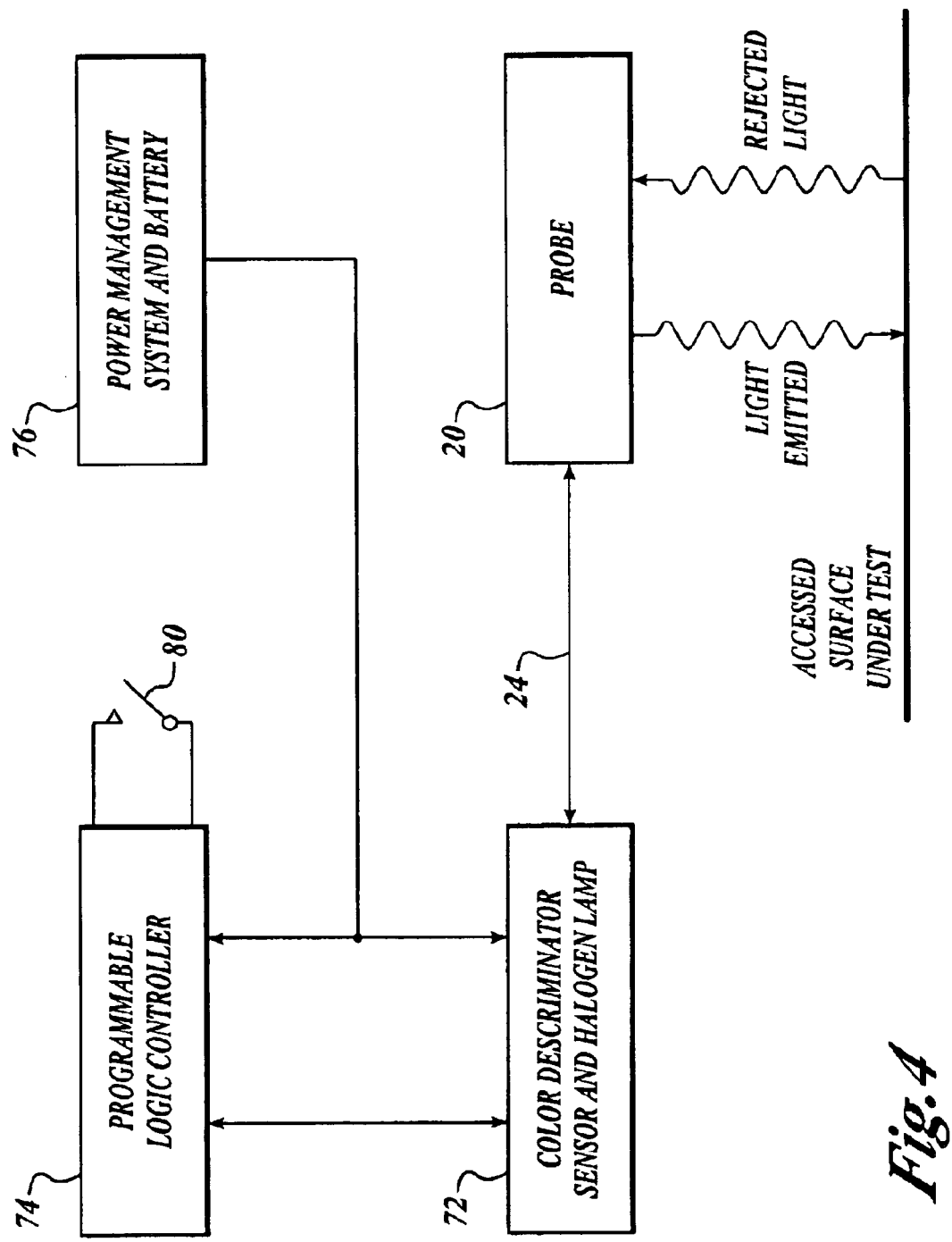
FIG. 4 is a block diagram of the present invention.

FIG. 4 is a block diagram of the present invention. The portable optical probe 20 emits light which is transmitted to the accessed surface. Reflected light is sensed by the probe 20. The probe 20 is in optical communication with a portable color discriminator 72 via the fiber-optic cable 24.

In one preferred embodiment, the color discriminator 72 is a color recognition fiberoptic sensor, such as a Keyence red-green-blue digital fiber-optic sensor. The color discriminator 72 performs color recognition based on color, not on target surface reflectivity. The color discriminator 72 separates reflected light into three primary color signals R (red), G (green), and B (blue), and converts each color signal into a digital value. In one preferred embodiment of the present invention, the color discriminator utilizes the color discrimination system described in U.S. Pat. No. 6,124,936 issued to Okamoto which is hereby incorporated by reference. The color discriminator 72 also includes an optical source, such as a halogen lamp or other acceptable light source, for providing light to the probe 20.

The color discriminator 72 is linked to a portable programmable logic controller 74 which decodes and permits display of information from the color discriminator 72. The logic controller 74 suitably allows the invention to be calibrated for different ranges of samples and different types of coatings being inspected. In one embodiment, calibration may be performed by sampling a pre-fabricated color or coatings chip or "coupon." The logic controller 74 analyzes and displays information from the color discriminator 72 thus informing an inspector when coatings have or have not been recognized. In one preferred embodiment, the logic controller 74 is a Keyence programmable logic controller Model No. KV-16 or Model No. KV-24 or the like. The logic controller 74 is activated by the test switch 80 when a test reading is to be taken by the inspector.

The present invention is powered by a portable power system 76 that is connected to the programmable logic controller 74 and the color discriminator 72. In one preferred embodiment, the power system includes a battery and a battery holder. Power is suitably provided by a rechargeable 14-volt DC lithium-ion battery. Power is converted to 24 volts VDC for use by the logic controller 74 and the color discriminator 72. In this embodiment, the battery can operate continuously for approximately four hours and can be recharged in about 1½ hours. The battery suitably has a power status LED (not shown). The power status LED illuminates to indicate that the battery has a sufficient charge. It will be appreciated that any suitable power source can be utilized to power the present invention, including a power cable to an external power source.

Figure 5:
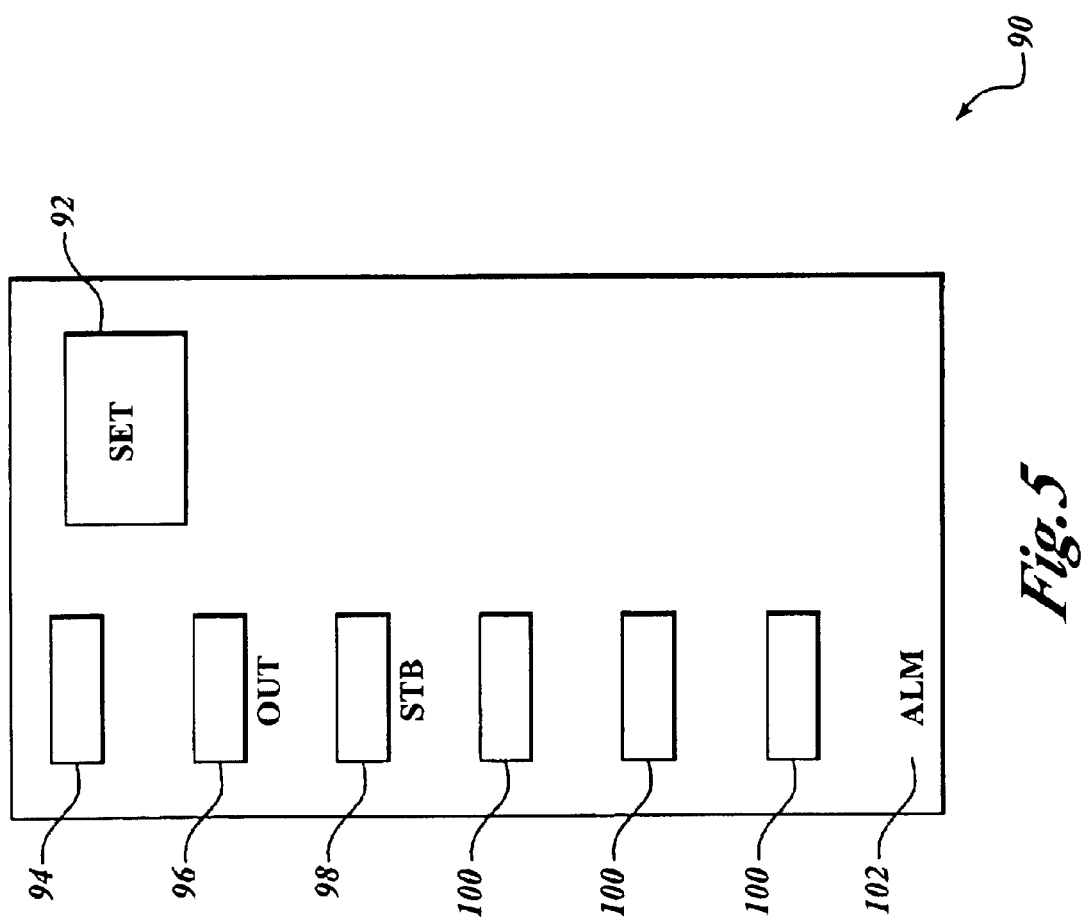
FIG. 5 is a view of an output display of the present invention.

FIG. 5 shows a display panel 90 of one preferred embodiment of the present invention. The display panel 90 allows programming and displaying information from the logic controller 74 (not shown). The display panel 90 has a set button 92 for setting the programming of the programmable logic controller to recognize particular coatings. One exemplary method to program the present invention to recognize specific coatings includes sensing premade color coupons. Programming is activated by depressing the set button 92. The display panel 90 also includes a calibration indicator 94 for indicating the invention has been calibrated. The display panel 90 includes an output indicator 96 for indicating the invention is prepared to provide output information. The display panel 90 also includes a stability indicator 98 which indicates whether the output received by the invention is stable. The logic controller 90 has at least one output channel 100 for displaying whether a coating has been identified by the present invention. In the embodiment shown in FIG. 5, the display panel 90 has three output channels 100 and an alarm indicator 102. The alarm indicator 102 may indicate difficulties with the power system or other anomalies in obtaining and displaying proper sensing information.

Figure 6:
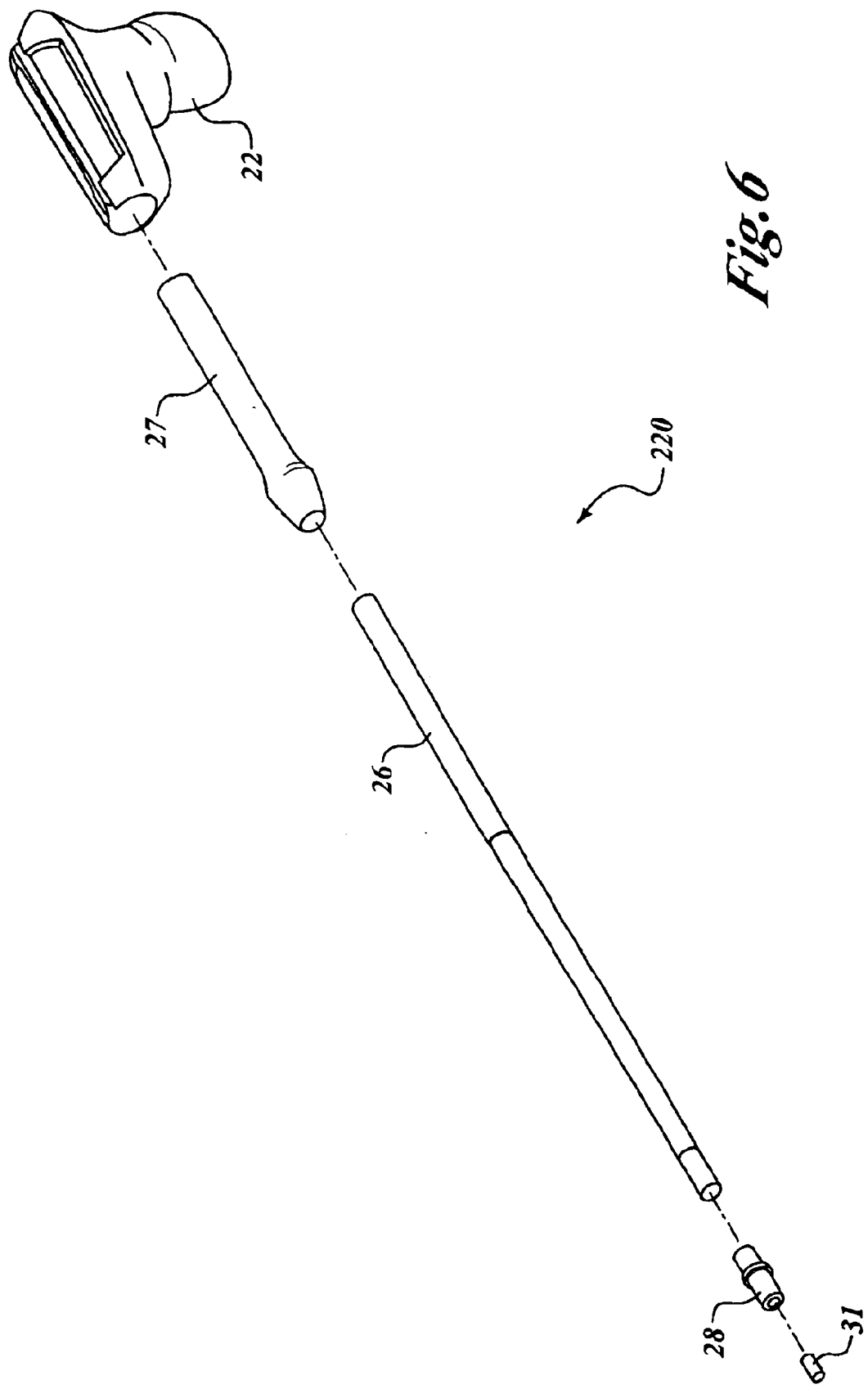
FIG. 6 is an isometric exploded view of an alternate portable optical probe of the present invention.

FIG. 6 shows an alternate embodiment of a portable optical probe 220. The probe 220 includes a handle 22, and a telescope holder 27 for the telescopic extension 26. The telescopic extension 26 is shown in the extended position. The telescopic extension 26 may be extended or collapsed by the inspector to permit inspection of different hard-to-reach areas. The telescopic extension 26 is attached to the sensor tip 28. In this embodiment, the sensor tip 28 holds a sensor lens 31 which is in optical communication with the fiber-optic cable 24 which connects the probe 20 to the color discriminator 72.

Figure 7:
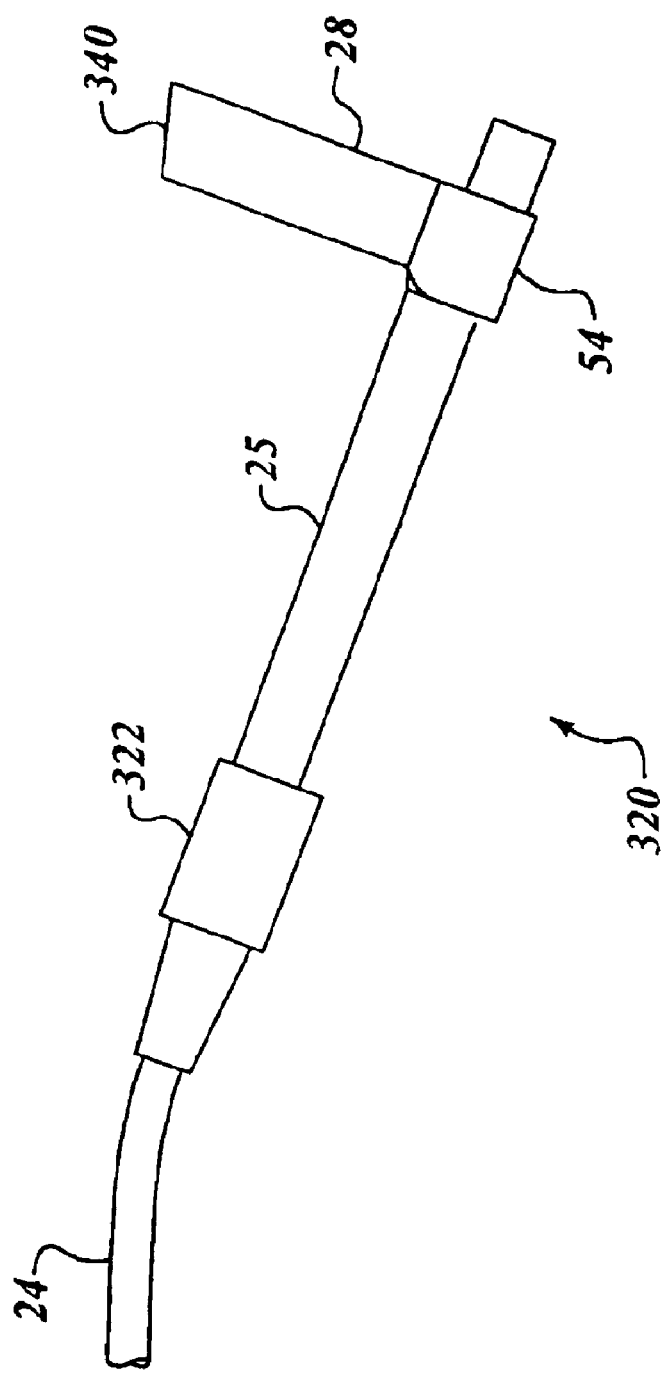
FIG. 7 is a side view of a another alternate portable optical probe with a 90 degree sensor tip.

FIG. 7 shows another alternate embodiment of a portable optical probe 320—in this instance a fixed 90 degree probe. The portable optical probe 320 has a handle 322 connected to a fixed extension 25. The fixed extension 25 is connected to a fixed right angle deflector 54 which is connected to the sensor tip 28. In this embodiment, the sensor tip 28 has an inclined sensor rim 340 which helps to position the sensor at an angle to the accessed surface (not shown). It will be appreciated that a variety of materials, configurations, and light conductors may be utilized for the fixed extension 25, the fixed right angle deflector 54 and the sensor tip 28, so long as optical communication is maintained between the fiber-optic cable 24 and the accessed surface. It will also be appreciated that various lengths of extensions and sensor tips, in various angles of deflection, will permit the present invention to be conveniently used in differently shaped areas. It will also be appreciated that a flexible or bendable extension would permit the inspector to configure the probe 320 to a desired shape at the test location.

Figure 8A:
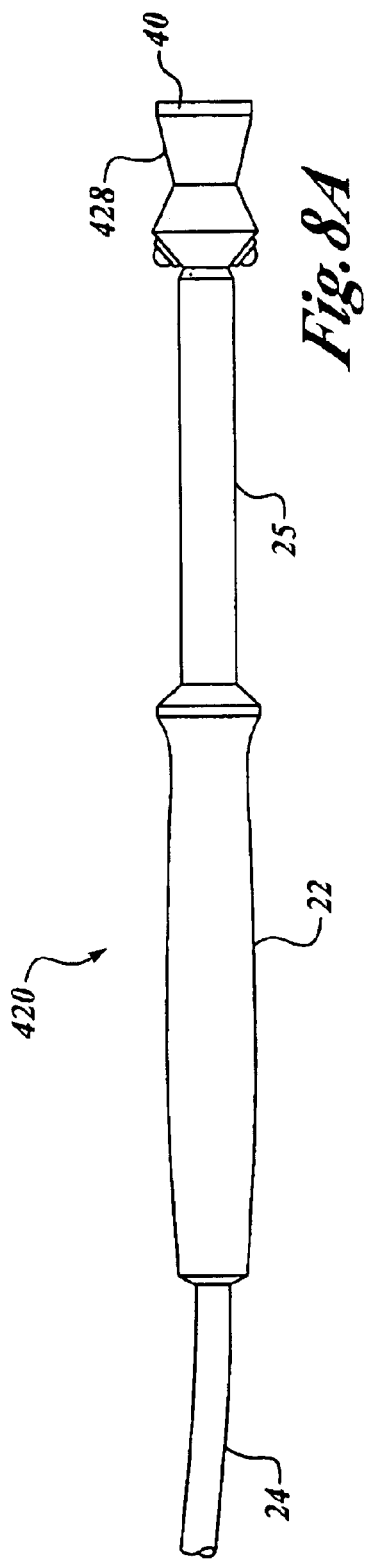
FIGS. 8A and 8B are a side view and a cross-section of a further alternate portable optical probe with indicator lights.
Figure 8B:
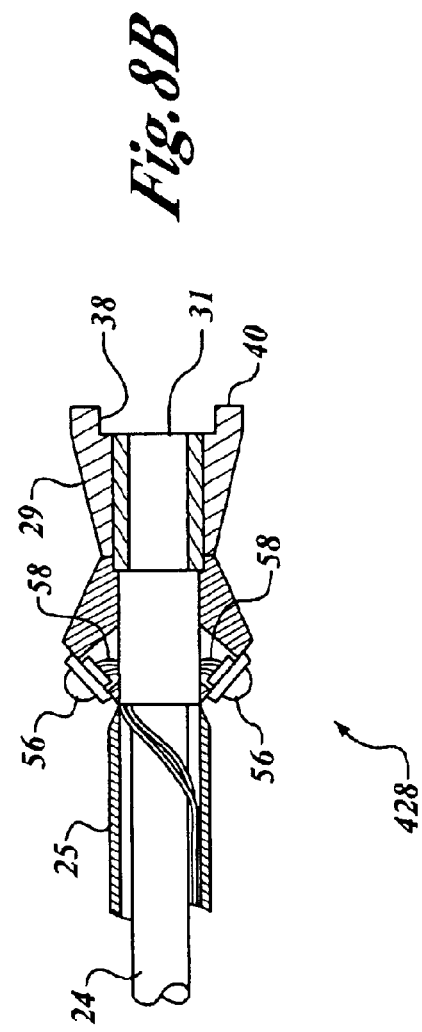

FIG. 8A shows another embodiment of a portable optical probe 420. The probe 420 is in optical communication with the color discriminator 72 via the fiber-optic cable 24. The fiber-optic cable 24 is threaded through the handle 22 and through a fixed extension 25 and is connected to a sensor tip 428. In this embodiment, the sensor tip 28 is fixed to, and is linearly aligned with, the extension 25 and handle 22. The handle 422 is not pistol-grip shaped, but is screwdriver handle shaped. FIG. 8B is a cross-section of the sensor tip 428. The fiber-optic cable 24 is routed to the sensor tip 428 through the fixed extension 25 and is in optical communication with the sensor lens 31. The sensor tip 428 includes a machined or molded sensor head 29 which holds the sensor lens 31 and is attached to the fixed extension 25. The sensor head 29 in this embodiment also holds probe indicator lights 56 which are connected to the programmable logic controller 74 through probe light wires 58. The probe indicator lights 56 indicate recognition of known coatings by the present invention directly on the probe 420. In one embodiment of the invention, one of the probe indicator lights 56 is green and one is red, with green indicating the presence of the desired coating and red indicating that no coating was recognized by the invention. The sensor rim 40 and sensor recess 38 permit the sensor lens 31 to be held at a fixed distance and fixed angle from the accessed surface (not shown). The sensor rim 40 is not inclined, so the sensor lens 31 is held perpendicular to the accessed surface. The sensor lens 31 is recessed into the sensor head 29 with the sensor recess 38 that holds the sensor lens 31 at a fixed desired distance from the accessed surface when the probe is pressed against the accessed surface.

The invention operates as follows: A coatings inspector carries the portable optical probe to the surface to be accessed, and then presses the probe against the accessed surface. The portable probe emits light into the accessed surface, and receives reflected light from the accessed surface depending upon the type and presence of a coating on the access surface, the reflected light has a particular spectrum, or colors. A portable color discriminator in optical communication with the portable optical probe discriminates the colors of the reflected light. Output from the color discriminator is then analyzed to determine the presence, or lack thereof, of a coating on the accessed surface. The portable optical probe may suitably include flexible, telescopic, pivoting, angled or detachable tips, permitting the inspector to flex, extend, pivot, or otherwise configure the probe to access hard-to-reach or hidden accessed surfaces. The system may be calibrated with precoated color coupons. This inspection method is especially useful for accessing aircraft components and inspecting for corrosion inhibitor compound.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined by reference to the claims that follows.

What is claimed is:

1. A portable system for inspecting presence of a coating on a surface, the system comprising:
   a portable optical source;
   a portable optical probe in optical communication with the optical source, the portable optical probe including a sensor tip having a rim engageable with the surface and an optical component at least partially disposed within the sensor tip, the rim being sized to space apart the optical component from the surface by a selected distance, the portable optical probe further being arranged to emit light onto the surface, and receive light reflected from the surface;
   a portable color discriminator in optical communication with the portable optical probe, the portable color discriminator being arranged to discriminate colors of the light received by the portable optical probe; and
   a portable controller that is arranged to determine presence of the coating on the surface responsive to the discriminated colors of the reflected light.

2. The system of claim 1, wherein the portable optical probe includes a telescopic extension.

3. The system of claim 1, wherein the portable optical probe includes an angled sensor tip.

4. The system of claim 1, wherein the portable optical probe includes a pivoting sensor tip.

5. The system of claim 1, wherein the portable optical probe includes a flexible positionable sensor tip.

6. The system of claim 1, further comprising:
   a carrier pack arranged to carry the portable optical source, the portable optical probe, the portable color discriminator, and the portable controller.

7. The system of claim 1, further comprising a portable power system arranged to provide power to the portable optical source, the portable color discriminator, and the portable controller.

8. The system of claim 1, wherein the portable optical probe includes indicator lights.

9. The system of claim 1, wherein the portable optical probe includes a removable handle.

10. A method for inspecting presence of a coating on a surface, the method comprising:
    accessing the surface with a portable optical probe wherein the accessed surface is an aircraft component;
    emitting light from the portable probe onto the accessed surface;
    receiving with the portable probe light reflected by the accessed surface;
    discriminating colors of the reflected light with a portable color discriminator; and
    determining presence of the coating on the accessed surface by analyzing the discriminated colors of the reflected light from the accessed surface, wherein the coating is a corrosion inhibitor compound.

11. The method of claim 10, wherein accessing with a portable probe includes:
    extending the portable optical probe telescopically.

12. The method of claim 10, wherein accessing with a portable probe includes:
    pivoting a pivot tip on the portable optical probe.

13. The method of claim 10, wherein accessing with a portable probe includes:
    flexing the portable optical probe.

14. The method of claim 10, wherein accessing with a portable probe includes:
    detaching a handle from the portable optical probe.

15. The method of claim 10, further comprising:
    calibrating the portable color discriminator using a color coupon.

16. The method of claim 10, further comprising:
    indicating presence of a coating on the accessed surface using a display.

17. The method of claim 10, wherein:
    accessing the surface with a portable optical probe includes accessing the surface with a portable optical probe including a sensor tip having a rim engageable with the surface and an optical component at least partially disposed within the sensor tip, the rim being sized to space apart the optical component from the surface by a selected distance.

18. A portable optical sensor probe, the probe comprising:
    an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;
    a fiber optic cable connected to the optical sensor tip;
    a handle connected to the optical sensor tip; and
    a telescopic extension connected to the handle and to the optical sensor tip.

19. A portable optical sensor probe, the probe comprising:
    an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;
    a fiber optic cable connected to the optical sensor tip; and
    a handle connected to the optical sensor tip, wherein the optical sensor tip is connected to the handle at an angle to the handle.

20. A portable optical sensor probe, the probe comprising:

an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;

a fiber optic cable connected to the optical sensor tip; and a handle connected to the optical sensor tip, wherein the optical sensor tip is pivotably connected to the handle.

21. A portable optical sensor probe, the probe comprising:

an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;

a fiber optic cable connected to the optical sensor tip; and a handle connected to the optical sensor tip, wherein the optical sensor tip is flexibly connected to the handle.

22. A portable optical sensor probe, the probe comprising:

an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;

a fiber optic cable connected to the optical sensor tip; and a handle connected to the optical sensor tip, wherein the handle is detachably connected to the optical sensor tip.

23. A portable optical sensor probe, the probe comprising:

an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance;

a fiber optic cable connected to the optical sensor tip;

a handle connected to the optical sensor tip; and further comprising indicator lights arranged to display test information to a user.

24. A portable optical sensor probe, the probe comprising:

an optical sensor tip arranged to transmit emitted light and to receive returned light, the optical sensor tip including a rim member engageable with a surface and an optical component at least partially disposed within the optical sensor tip, the rim member being sized to space apart the optical component from the surface by a selected distance, wherein the optical sensor tip includes an end portion pivotably coupled to a holder portion, the end portion being pivotable between a first position wherein a first longitudinal axis of the end portion is substantially parallel with a second longitudinal axis of the holder portion, and a second position wherein the first longitudinal axis is substantially perpendicular with the second longitudinal axis;

a fiber optic cable connected to the optical sensor tip; and a handle connected to the optical sensor tip.

* * * * *